US00PP25413P2

(12) United States Plant Patent
Hill et al.

(10) Patent No.: US PP25,413 P2
(45) Date of Patent: Apr. 7, 2015

(54) ***HYDRANGEA* PLANT NAMED 'BROTHER EDWARD'**

(50) Latin Name: *Hydrangea quercifolia*
Varietal Denomination: Brother Edward

(71) Applicants: Doug Hill, Cleveland, AL (US); Brenda Hill, Cleveland, AL (US)

(72) Inventors: Doug Hill, Cleveland, AL (US); Brenda Hill, Cleveland, AL (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/987,722

(22) Filed: Aug. 23, 2013

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

PUBLICATIONS

UPOV hit on PLUTO: Plant Variety Database for *hydrangea* named Brother Edward, publication date Oct. 31, 2012.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'Brother Edward', characterized by its compact, upright and outwardly spreading plant habit; vigorous growth habit; strong and sturdy stems; long flowering period; and large inflorescences with white-colored flowers.

1 Drawing Sheet

Botanical designation: *Hydrangea quercifolia.*
Cultivar denomination: 'BROTHER EDWARD'.

BACKGROUND OF THE INVENTION

The present invention relates to a new and distinct *Hydrangea* plant, botanically known as *Hydrangea quercifolia* and hereinafter referred to by the name 'Brother Edward'.

The new *Hydrangea* plant is a product of a planned breeding program conducted by the Inventors in Cleveland, Ala. The objective of the breeding program was to develop new *Hydrangea* plants with interesting inflorescence forms.

The new *Hydrangea* plant originated from an open-pollination in 1988 of an unnamed seedling selection of *Hydrangea quercifolia*, not patented, as the female, or seed parent with an unknown selection of *Hydrangea quercifolia* as the male, or pollen, parent. The new *Hydrangea* plant was discovered and selected by the Inventors as a single flowering plant from within the progeny of the stated open-pollination in a controlled environment in Cleveland, Ala. in 1993.

Asexual reproduction of the new *Hydrangea* plant by softwood cuttings in a controlled environment in Cleveland, Ala. since July, 2004 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Brother Edward'. These characteristics in combination distinguish 'Brother Edward' as a new and distinct *Hydrangea* plant:

1. Compact, upright and outwardly spreading plant habit.
2. Vigorous growth habit.
3. Strong and sturdy stems.
4. Long flowering period.
5. Large inflorescences with white-colored flowers.

Plants of the new *Hydrangea* differ from plants of the female parent selection in the following characteristics:

1. Inflorescences of plants of the new *Hydrangea* are denser than inflorescences of plants of the female parent selection.
2. Flowers of plants of the new *Hydrangea* become green with age whereas flowers of plants of the female parent selection become pink with age.
3. Plants of the new *Hydrangea* do not produce seed whereas plants of the female parent selection produce seed.

Plants of the new *Hydrangea* can be compared to plants of *Hydrangea quercifolia* 'Harmony', not patented. In side-by-side comparisons, plants of the new *Hydrangea* differed primarily from plants of 'Harmony' in the following characteristics:

1. Plants of the new *Hydrangea* were more compact than plants of 'Harmony'.
2. Inflorescences of plants of the new *Hydrangea* were more rain-tolerant than inflorescences of plants of 'Harmony'.

BRIEF DESCRIPTION OF THE PHOTOGRAPH

The accompanying colored photograph illustrates the unique appearance of the new *Hydrangea* plant showing the colors as true as it is reasonably possible to obtain in colored reproductions of this type. Colors in the photograph may differ from the color values cited in the detailed botanical description which accurately describe the colors of the new *Hydrangea* plant.

The photograph comprises a top perspective view of a typical flowering plant of 'Brother Edward'.

DETAILED BOTANICAL DESCRIPTION

Plants used for the aforementioned photographs and the following description were grown during the summer in three-gallon containers in an outdoor nursery in Grand Haven, Mich. and under cultural practices typical of commercial *Hydrangea* production. Plants of the new *Hydrangea* were three years old when the photographs and description were taken. In the following description, color references are made to The Royal Horticultural Society Colour Chart, 2001 Edition, except where general terms of ordinary dictionary significance are used.

Botanical description: *Hydrangea quercifolia* 'Brother Edward'.

Parentage:

*Female, or seed, parent*.—Unnamed seedling selection of *Hydrangea quercifolia*, not patented.

*Male, or pollen, parent*.—Unknown selection of *Hydrangea quercifolia*, not patented.

Propagation:

*Type cutting*.—By softwood cuttings.

*Time to initiate roots, summer*.—About 28 days at temperatures of about 24° C.

*Time to produce a rooted young plant, summer*.—About four months at temperatures of about 24° C.

*Root description*.—Fine, fibrous; white in color.

*Rooting habit*.—Freely branching; dense.

Plant description:

*Plant form and growth habit*.—Perennial deciduous shrub; relatively compact, upright and outwardly spreading plant habit; broad inverted triangle; strong and sturdy lateral branches; freely branching habit with about five lateral branches per plant; vigorous growth habit.

*Plant height*.—About 38 cm.

*Plant diameter or area of spread*.—About 57 cm.

*Lateral branches*.—Length: About 34 cm. Diameter: About 5 mm. Internode length: About 4 cm. Texture: Pubescent. Strength: Strong, sturdy. Color: Close to 164A; with development becoming closer to 200A.

Leaf description:

*Arrangement*.—Opposite, simple.

*Length*.—About 9.5 cm.

*Width*.—About 8.5 cm.

*Shape*.—Ovate.

*Apex*.—Acuminate.

*Base*.—Obtuse.

*Margin*.—Palmately lobed.

*Texture, upper surface*.—Leathery; pubescent.

*Texture, lower surface*.—Coarse; pubescent.

*Venation pattern*.—Palmate.

*Color*.—Developing leaves, upper surface: Close to 145A. Developing leaves, lower surface: Close to 147D. Fully expanded leaves, upper surface: Close to 137A; venation, close to 166C. Fully expanded leaves, lower surface: Close to 148B; venation, close to 165B.

*Petioles*.—Length: About 5 cm. Diameter: About 2 mm. Texture, upper and lower surfaces: Pubescent. Color, upper surface: Close to 166C. Color, lower surface: Close to 165B.

Flower description:

*Flower type and habit*.—Single sterile flowers arranged on large terminal mophead-type panicles; no fertile flowers observed; flowers face upright or outwardly.

*Fragrance*.—Mildly fragrant; pleasant.

*Natural flowering season*.—Plants flower continuously throughout the summer in Grand Haven, Mich.

*Quantity of flowers*.—Freely flowering habit; about 256 sterile flowers per inflorescence.

*Inflorescence height*.—About 11 cm.

*Inflorescence diameter*.—About 9 cm.

*Flower diameter*.—About 2.8 cm.

*Flower depth (height)*.—About 5 mm.

*Flower buds*.—Length: About 2 mm. Diameter: About 1 mm. Shape: Elliptic. Color: Close to 145B.

*Petals*.—Not observed.

*Sepals*.—Quantity per flower: Four in a single whorl. Length: About 1.3 cm. Width: About 1.4 cm. Shape: Orbicular. Apex: Obtuse. Base: Obtuse. Margin: Entire. Texture, upper surface: Smooth, glabrous. Texture, lower surface: Coarse, glabrous. Color: When opening, upper and lower surfaces: Close to 145D. Fully opened, upper and lower surfaces: Close to 155C; flowers becoming green with age.

*Pedicels*.—Angle: About 40° to 50° from inflorescence axis. Strength: Strong, sturdy. Length: About 1.5 cm. Diameter: About 1 mm. Texture: Smooth. Color: Close to 145D.

*Reproductive organs*.—Stamens: Quantity per flower: About six. Filament length: About 1 mm. Filament color: Close to 145D. Anther shape: Round. Anther length: About 0.5 mm. Anther color: Close to 155B. Pollen amount: None observed. Pistils: Pistil quantity per flower: One. Pistil length: About 2 mm. Stigma shape: Round. Stigma color: Close to 145C. Style length: About 1 mm. Style color: Close to 145C. Ovary color: Close to 145D.

*Seeds*.—Seed development has not been observed on plants of the new *Hydrangea*.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures ranging from about −16° C. to about 44° C.

It is claimed:

1. A new and distinct *Hydrangea* plant named 'Brother Edward' as illustrated and described.

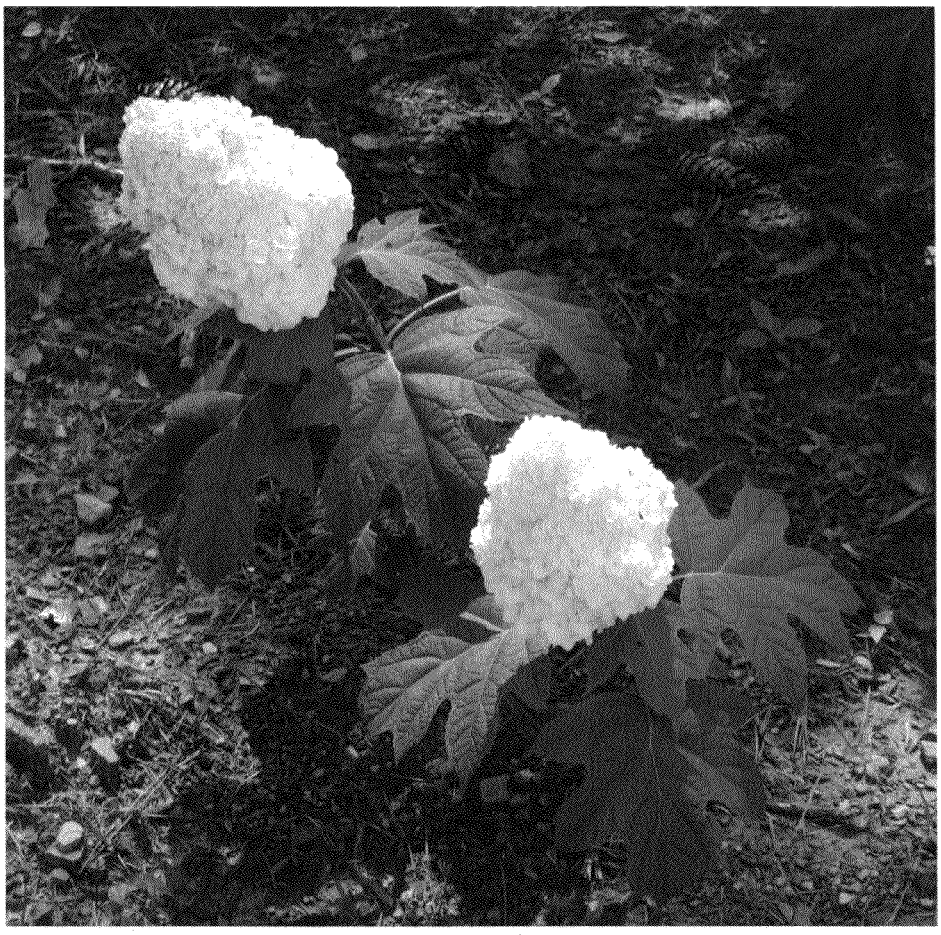

* * * * *